United States Patent [19]

Van Rheenen

[11] Patent Number: 4,501,695

[45] Date of Patent: Feb. 26, 1985

[54] SPIRONALACTONE PROCESS

[75] Inventor: Verlan H. Van Rheenen, Portage, Mich.

[73] Assignee: The Upjohn Company, Kalamazoo, Mich.

[21] Appl. No.: 494,740

[22] Filed: May 16, 1983

[51] Int. Cl.³ ............................................ C07J 19/00
[52] U.S. Cl. .......................... 260/239.57; 260/239.5; 260/239.55 R; 260/239.55 C; 260/397.5
[58] Field of Search ............. 260/239.57, 397.5, 239.5, 260/239.55

[56] References Cited

U.S. PATENT DOCUMENTS

| | | | |
|---|---|---|---|
| 2,900,383 | 8/1959 | Cella | 260/239.57 |
| 3,013,012 | 12/1961 | Cella et al. | 260/239.57 |
| 3,413,288 | 11/1968 | Creger | 260/239.57 |
| 3,452,008 | 6/1969 | Buzby, Jr. et al. | 260/239.57 |
| 3,682,894 | 8/1972 | Dryden, Jr. | 260/239.57 |
| 3,847,906 | 11/1974 | Radscheit et al. | 260/239.55 |
| 3,883,512 | 5/1975 | Stache et al. | 260/239.57 |
| 3,894,006 | 7/1975 | Stache et al. | 260/239.55 R |
| 3,897,417 | 7/1975 | Warnant et al. | 260/239.57 |
| 3,900,467 | 8/1975 | Irmscher et al. | 260/239.55 C |
| 3,966,714 | 6/1976 | Philippson | 260/239.57 |
| 4,057,543 | 11/1977 | Dryden, Jr. et al. | 260/239.57 |
| 4,211,701 | 7/1980 | Timko | 260/239.57 |
| 4,267,106 | 5/1981 | Marx et al. | 260/239.57 |
| 4,396,614 | 8/1983 | Nedelec et al. | 260/239.57 |

FOREIGN PATENT DOCUMENTS 878259 8/1979 Belgium .
2028825 8/1979 United Kingdom .

OTHER PUBLICATIONS

Sturtz, Georges, et al., Lactonization at the 17β-Position of Steroids, Synthesis, 289–291, Apr. 1980.

Toye, José, et al., Synthesis and Reactivity of α-Cyanoenamines, A Novel General Method for Preparing α-Diketones from Amides, J.A.C.S., 97:8, 2276–2277, Apr. 16, 1975.

Lesur, Brigitte, et al., Base-Catalysed Alkylations and Conjugated Additions of α-Cyanoenamines: A Method for Chain Extension at the β-Carbon of Tertiary Amides, Tetrahedron Letters No. 30, 2835–2838, (1979).

Ahlbrecht, H., et al., 3-Metallierte Enamine; IV[1]. Metallierung von 1-Cyanoenaminen, eine einfache Methode zur Erzeugung von 3-Carboxy-carbanionen, Synthesis, 512–515, Mar. 1975.

Ahlbrecht, H., et al., Eine einfache Methode zur Herstellung von 1-Phosphonatoenaminen, Synthesis, 336–338, Jan. 1977.

*Primary Examiner*—Elbert L. Roberts
*Attorney, Agent, or Firm*—William G. Jameson

[57] ABSTRACT

The present invention relates to processes for the conversion of a 3-protected steroidal 17-ketone to a 17-spiro-γ-lactone having the appropriate 17-stereochemistry for spironolactone. Novel intermediates (II, II', II'', II''', II$^a$, II$^b$, II$^c$, II$^d$, II$_x$, II'$_x$ and II''$_x$) are also disclosed.

45 Claims, No Drawings

SPIRONALACTONE PROCESS

BACKGROUND OF THE INVENTION

7-β-Acetylthio-17β-(2-carboxyethyl)-17β-hydroxyandrost-4-en-3-one lactone (spironolactone) is a diuretic marketed both alone and with another diuretic (hydrochlorothiazide). See the Physicians Desk Reference 1978, pages 1537 and 1538, respectively.

A number of methods for the synthesis of spironolactone are known, see for example, U.S. Pat. Nos. 3,013,012, 3,413,288, 3,682,894, 3,847,906, 3,883,512, 3,894,006, 3,897,417, 3,900,467, 3,966,714, 4,057,543 and 4,211,701. These patents report multistep processes for the conversion of a steroidal-17-ketone to the 17α-(2-carboxyethyl)-17β-hydroxyandrost-4-en-3-one lactone (hereinafter referred to as 17-spirolactone). The transformation of 17-spirolactone to the 17α-(2-carboxyethyl)-17β-hydroxyandrosta-4,6-dien-3-one lactone (hereinafter referred to as Δ4,6-lactone) can be performed in a number of ways, see U.S. Pat. No. 3,452,008 for the transformation of a 19-nor lactone to the corresponding 19-nor-Δ4,6-lactone. In addition, U.S. Pat. No. 2,900,383 (Example 2) discloses the transformation of 17-spirolactone to the Δ4,6-lactone. U.S. Pat. No. 4,211,701 discloses the transformation of 17-spirolactone to the 3-acyloxy-17α-(2-carboxyethyl)-17β-hydroxyandrosta-3,5-diene lactone, bromination to give 6-bromo-17α-(2-carboxyethyl)-17β-hydroandrost-4-ene-3-one lactone and heating in the presence of calcium carbonate to give 17α-(2-carboxyethyl)-17β-hydroxyandrosta-4,6-dien-3-one lactone (Δ4,6-lactone).

The Δ4,6-lactone is transformed to spironolactone by methods well known to those skilled in the art, in particular, see U.S. Pat. No. 3,013,012 (Example 3) and U.S. Pat. No. 4,211,701 (Col. 8, lines 15–33).

U.S. Pat. No. 4,267,106, German Offenlegungsschrift No. 2,932,924, and British Application No. 2,028,825 describe a single step process for the conversion of a 3-protected androst-5-ene-17-one, to 17β-hydroxy-3-oxo-17α-pregn-4-ene-21-carboxylic acid γ-lactone (17-spirolactone) and 17β-hydroxy-3-oxo-17α-pregna-4,6-diene-21-carboxylic acid γ-lactone by reacting the ketone with organophosphorous compounds such as allyl phosphate bis-methyl and bis-diethyl-amide, allyl dimethyl phosphate and allyl diethyl phosphate, in an organic solvent at a temperature between −90° and +50° C. and in the presence of a suitable strong base, for example, alkyl- or aryl-lithium compounds.

See also Sturtz, et al., Lactonization at 17β-position of steroids, Synthesis, 289–291, April 1980. Sturtz describes the direct synthesis of andronolactone and its methyl homolog by reaction of the O-tetrahydropyranyl derivative of 3β-hydroxy-17-oxo-5-androstene with the dilithio derivative obtained from allyl or 2-methylallyl tetramethylphosphorodiamidate and 2 equiv of butyllithium.

Two groups of investigators have shown that 2-(disubstituted amino)-2-butenonitrile, on deprotonation, gives an anion which preferentially adds electrophiles exclusively in the γ-position, see Toye, et al., J.A.C.s., 97, 2276 (1975); Lesin, et al., Tetra. Lett., 2835 (1979); H. Albrecht, et al., Synthesis, 512 (1975) and H. Albrecht, et al., Synthesis, 336 (1977).

BRIEF DESCRIPTION OF THE INVENTION

Disclosed is a process for producing 17α-(2-carboxyethyl)-17β-hydroxyandrost-4-ene-3-one lactone and 17α-(2-carboxyethyl)-17β-hydroxyandrosta-4,6-diene-3-one lactone which comprises:

(1) treating a disubstituted nitrile of formula A or B with a deprotonating agent;

(2) reacting the resultant deprotonated nitrile with a 3-protected steroid 17-ketone (formula I) to give the amino nitrile adduct (formula II);

(3) acidifying the amino nitrile adduct (formula II) with an acid to form the imino lactone (formula III); and (4) neutralizing the imino lactone (formula III) with a base to give a 17-spiro-γ-lactone of formula I′.

Further disclosed is a process for producing spirolactone which comprises reacting a steroidal-17-ketone with a deprotonated disubstituted phosphonate enamine of formula C, D, E or F.

Also disclosed is a process for producing disubstituted phosphonate enamines of formulas C or E which comprises:

1. Preparation of imino chloride 2 by reaction of a propionamide 1 with phosgene.
2. Reaction of imino chloride 2 with a phosphite or an alkoxy phosphorus diamine to give C or E respectively. See Chart A.

DETAILED DESCRIPTION OF THE INVENTION

The present invention includes a process to produce spirolactone from 3-methoxy-17-oxo-3,5-androstadiene. This process is set forth in

CHART B.

3-Methoxy-17-oxo-3,5-androstadiene is dissolved in a suitable solvent and reacted with a deprotonated disubstituted amino nitrile of formula A or B, wherein $R_x$ and $R_y$ are the same or different and each represents alkyl of 1 to 5 carbon atoms, aryl of 6 thru 10 carbon atoms or substituted aryl, or $R_x$ and $R_y$ taken together form a 5-, 6- or 7-membered heterocyclic group, which may contain in the ring a further hetero atom, selected from the group consisting of nitrogen, oxygen or sulfur, preferably a dialkyl amino nitrile such as 2-diethyl amino-2-butenonitrile, in a suitable solvent at a low temperature. The reaction may be carried out under an inert atmosphere, e.g. under nitrogen. Solvents such as THF, dioxane and 1,2-dimethoxyethane can be used, however a solvent system such as ether/toluene is generally preferred. The reaction may be performed in the temperature range of −20° to −100°, preferably at −20°. The disubstituted amino nitrile (formula A or B) may be deprotonated by methods well known to those skilled in the art, preferably with an alkali metal amide such as lithium diethylamide, lithium diisopropylamide, lithium hexamethyldisilazide or the sodium or potassium salts of the foregoing amides, preferably a lithium amide base such as lithium diisopropylamide in etheral-like solvents such as THF, ethyl ether, 1,2-dimethoxyethane or dioxan, at a temperature of −10° to −50°, preferably −40°.

Neutralization of the reaction mixture and chromatography results in isolation of amino nitrile adduct (II), but it is preferred and more convenient to acidify the reaction mixture with acid. The particular acid is not critical, various acids suitable include hydrochloric, sulfuric, acetic, phosphoric, citric, benzoic, etc.

Following acidification, the water soluble amine salt of the adduct is removed from the unreacted stating material by extractive separation according to methods well known in the art. Neutralization of the acid aqueous phase with base gives spirolactone. The particular base is not critical, suitable bases included sodium hydroxide, sodium carbonate, and pyridine.

Similarly, by following in principle the process as described above, but substituting other appropriate 3-protected steroidal-17-ketones, for 3-methoxy-17-oxo-3,5-androstadiene, including, for example, steroids of the androstane series of the formula I: wherein (i) $R_1$ represents a group $-OR_4$ in which $R_4$ represents a hydrogen atom, an alkyl or alkoxyalkyl group or a group of formula H:

wherein $R_5$ represents a hydrogen atom or an alkyl group and $R_6$ represents an alkyl group or $R_5$ and $R_6$ together with the carbon and oxygen atoms in which they are attached represent a 5- or 6-membered heterocyclic group (e.g. tetrahydropyranyl) and $R_2$ and $R_3$ each represent a hydrogen atom; or (ii) $R_1$ and $R_2$ are the same or different and each represents a group $-OR_4$, wherein $R_4$ represents an alkyl group, or $R_1$ and $R_2$ together represent an alkylenedioxy group having 2 or 3 carbon atoms in the alkylene moiety, and $R_3$ represents a hydrogen atom, or (iii) $R_1$ represents a group $-OR_4$, or a group of formula J:

wherein $R_7$ and $R_8$ are the same or different and each represents an alkyl group, or $R_7$ and $R_8$ together with the nitrogen atom to which they are attached represent a 5- or 6-membered heterocyclic group, (e.g. 1-pyrrolidyl), which may contain a further hetero atom in the ring (e.g. N-morpholinyl), and $R_2$ and $R_3$ together represent an additional bond in the 3-4 position; 17-spiro-$\gamma$-lactones of the formula I' can also be prepared.

The starting materials of formula I can be obtained from androst-4-ene-3,17-dione or from dehydro-epiandrosterone by methods well known in the art. See for example G. B. No. 2,028,825, page 3, line 67 thru page 4, line 41. See also J. L. Johnson, et al., J.A.C.S., 78, 230 (1956) for a method of preparing the starting materials of formula $I^c$.

In addition, the 3-protected androsta-4,6-diene-17-one derivative of the formula X, prepared by methods well known in the art. See for example, G. J. Fonken, et al., J. Org. Chem., 26 2549 (1961).

Appropriate 3-protected steroidal-17-ketones (I) include 3-enol ethers ($I^a$) and 5-ene-3-ol ethers ($I^b$) such as 3-methoxy-, 3-ethoxy-, 3-propoxy- or 3-butoxy-17-oxo-3,5-androstadiene ($I^a$), 3-methoxy-, 3-ethoxy-, 3-propoxy- or 3-butoxy-17-oxo-5-androstene ($I^b$); 3-enamines ($I^c$) such as 3-diethylamino-17-oxo-3,5-androstadiene, 3-(1'-pyrrolidino)-17-oxo-3,5-androstadiene, 3-(N-morpholinyl)-17-oxo-3,5-androstadiene; and 3-ketals ($I^d$) such as 3,3-ethylenedioxy-17-oxo-5-androstene. Aminonitrile adducts (II) include $II^a$, $II^b$, $II^c$ and $II^d$ and geometrical isomers thereof.

Similarly, by following in principle the process of the subject invention, but substituting disubstituted phosphonate enamines of formulas C, D, E or F; where R", R''', $R_x$ and $R_y$ are the same or different and each represents alkyl of 1 to 5 carbon atoms, aryl of 6 thru 10 carbon atoms or substituted aryl, or $R_x$ and $R_y$ or R" and R''' and R''' taken together form a 5-, 6- or 7-membered heterocyclic group, which may contain in the ring a further hetero atom, selected from the group consisting of nitrogen, oxygen or sulfur; including, for example:

dimethyl [1-(diethylamino)-1-propenyl]phosphonate (C)

dimethyl [1-(diethylamino)-2-propenyl]phosphonate (D)

p-[1-(diethylamino)-1-propenyl]-N,N,N',N'-tetramethylphosphonic diamide (E)

p-[1-(diethylamino)-2-propenyl]-N,N,N',N'-tetramethylphosphonic diamide (F)

dimethyl [1-(1'-pyrrolidino)-1-propenyl]phosphonate (C)

dimethyl [1-(1'-pyrrolidino)-2-propenyl]phosphonate (D)

p-[1-(1'-pyrrolidino)-1-propenyl]-N,N,N',N'-tetramethylphosphonic diamide (E)

p-[1-(1'-pyrrolidino)-2-propenyl]-N,N,N',N'-tetramethylphosphonic diamide (F)

dimethyl [1-(1'-piperidino)-1-propenyl]phosphonate (C)

dimethyl [1-(1'-piperidino)-2-propenyl]phosphonate (D)

p-[1-(1'-piperidino)-1-propenyl]-N,N,N',N'-tetramethylphosphonic amide (E)

p-[1-(1'-piperidino)-2-propenyl]-N,N,N',N'-tetramethylphosphonic diamide (F)

dimethyl [1-(N-morpholino)-1-propenyl]phosphonate (C)

dimethyl [1-(N-morpholino)-2-propenyl]phosphonate (D)

p-[1-(N-morpholino)-1-propenyl]-N,N,N',N'-tetramethylphosphonic diamide (E)

p-[1-(N-morpholino)-2-propenyl]-N,N,N',N'-tetramethylphosphonic diamide (F)

dimethyl [1-(N-methylanilino)-1-propenyl]phosphonate (C)

dimethyl [1-(N-methylanilino)-2-propenyl]phosphonate (D)

p-[1-(N-methylanilino)-1-propenyl]-N,N,N'-N'-tetramethylphosphonic diamide (E)

p-[1-(N-methylanilino)-2-propenyl]-N,N,N',N'-tetramethylphosphonic diamide (F)

and the like, for the disubstituted amino nitrile (formula A or B), 17α-(2-carboxyethyl)-17β-hydroxy lactones are prepared by acidifying the phosphate enamine adduct with an acid to give a spiro-γ-lactone of formula I'. See Chart C. For example, 3-methoxy-17-oxo-3,5-androstadiene is dissolved in a suitable solvent and reacted with a deprotonated disubstituted phosphonate enamine in a suitable solvent at a low temperature. The reaction may be carried out under an inert atmosphere, e.g. under nitrogen. Solvents such as THF, dioxane, dimethoxyethane, ethylether, and toluene can be used, preferably THF. The reaction may be performed in the temperature range of $-10°$ to $-78°$. The disubstituted phosphate enamine (formula C, D, E or F) may be deprotonated by methods well known to those skilled in the art, preferably with a lithium amide base such as lithium diisopropylamide in etheral-like solvents such as THF, dioxane, dimethoxyethane, ethylether, or toluene, at a temperature of $-10°$ to $-78°$.

Neutralization of the reaction mixture and chromatography results in isolation of the corresponding adduct II' or II", but is is preferred and more convenient to acidify the reaction mixture with acid extract II' or II" and hydrolyze, to yield 17-spirolactone.

Phosphonate enamines of formula C and E can be prepared according to the method of H. Albrecht, et al., Synthesis, 336 (1977).

Similarly, by following in principle the processes as described above, the 3-ketal androsta-4,6-diene-17-one derivatives of formula X, wherein $R_9$ and $R_{10}$ are the same or different and each represents a group $—OR_4$, wherein $R_4$ represents an alkyl group, or $R_9$ and $R_{10}$ together represent an alkylenedioxy group having 2 or 3 carbon atoms in the alkylene moiety; can be reacted with a deprotonated disubstituted nitrile of formula A or B or a disubstituted phosphonate enamine of formula C, D, E or F to obtain the Δ4,6-lactone of the formula X'.

Illustrative disubstituted amino nitriles of formula A and B include:
2-diethylamino-2-butenonitrile
2-diethylamino-3-butenonitrile
2-dimethylamino-2-butenonitrile
2-dimethylamino-3-butenonitrile
2-(1'-pyrrolidino)-3-butenonitrile
2-(1'-piperidino)-3-butenonitrile
2-(N-morpholino)-3-butenonitrile
2-(N-methylanilino)-3-butenonitrile.

Illustrative amino nitrile adducts (II) include:
17α-[3-diethylamino)-3-cyano-2-propenyl]-17β-hydroxy-3-methoxy-3,5-androstadiene
17α-[3-(dimethylamino)-3-cyano-2-propenyl]-17β-hydroxy-3-methoxy-3,5-androstadiene
17α-[3-(1'-pyrrolidino)-3-cyano-2-propenyl]-17β-hydroxy-3-methoxy-3,5-androstadiene
17α-[3-(1'-piperidino)-3-cyano-2-propenyl]-17β-hydroxy-3-methoxy-3,5-androstadiene
17α-[3-(N-morpholino)-3-cyano-2-propenyl]-17β-hydroxy-3-methoxy-3,5-androstadiene
17α-[3-(1'-hexahydroazepinyl)-3-cyano-2-propenyl]-17β-hydroxy-3-methoxy-3,5-androstadiene
17α-[3-(N-methylanilino)-3-cyano-2-propenyl]-17β-hydroxy-3-methoxy-3,5-androstadiene.

Illustrative phosphonate enamine adducts (II') include:
17α-[3-(diethylamino)-3-[bis(diethylamino)phosphonyl]-2-propenyl]-17β-hydroxy-3-methoxy-3,5-androstadiene
17α-[3-(1'-pyrrolidino)-3-[bis(diethylamino)phosphinyl]-2-propenyl]-17β-hydroxy-3-methoxy-3,5-androstadiene
17α-[3-(1'-piperidino)-3-[bis(diethylamino)phosphinyl]-2-propenyl]-17β-hydroxy-3-methoxy-3,5-androstadiene
17α-[3-(N-morpholino)-3-[bis(diethylamino)phosphinyl]-2-propenyl]-17β-hydroxy-3-methoxy-3,5-androstadiene
17α-[3-(N-methylanilino)-3-[bis(diethylamino)phosphinyl]-2-propenyl]-17β-hydroxy-3-methoxy-3,5-androstadiene.

Illustrative phosphonic diamide enamines (II) include:
17α-[3-(diethylamino)-3-(dimethoxyphosphinyl)-2-propenyl]-17β-hydroxy-3-methoxy-3,5-androstadiene
17α-[3-(1'-pyrrolidino)-3-(dimethoxyphosphinyl)-2-propenyl]-17β-hydroxy-3-methoxy-3,5-androstadiene
17α-[3-(1'-piperidino)-3-(dimethoxyphosphinyl)-2-propenyl]-17β-hydroxy-3-methoxy-3,5-androstadiene
17α-[3-(N-morpholino)-3-(dimethoxyphosphinyl)-2-propenyl]-17β-hydroxy-3-methoxy-3,5-androstadiene
17α-[3-(N-methylanilino)-3-(dimethoxyphosphinyl)-2-propenyl]17β-hydroxy-3-methoxy-3,5-androstadiene.

DEFINITIONS

The definitions and explanations below are for the terms as used throughout the entire patent application including both the specification and claims.

All temperatures are in degrees Centigrade.
TLC refers to thin-layer chromatography.
THF refers to tetrahydrofuran.
DMF refers to dimethylformamide.
NMR refers to nuclear (proton) magnetic resonance spectroscopy, chemical shifts are reported in ppm (δ) downfield from TMS.
MS refers to mass spectroscopy.
Ether refers to diethyl ether.
The term $X^-$ refers to the negatively charged atom of the addition salt.
The term "alkyl of 1 thru 5 carbon atoms" is used to include the isomers thereof when they exist.
The term "substituted aryl" means aryl of 6 to 10 carbon atoms substituted with 1 to 3 substituents selected from the groups consisting of lower alkyl-, lower alkoxy-, halogen-, nitro-, and cyano-, preferably substituted phenyl. There can be combinations of substituents.
Phosphate Buffer refers to an aqueous solution 5% in $KH_2PO_4$ and 5% in $K_2HPO_4$.

EXAMPLES

Without further elaboration, it is believed that one skilled in the art can, using the preceding description, practice the present invention to its fullest extent. The following preferred specific embodiments are, therefore, to be construed as merely illustrative, and not limiting of the preceding disclosure in any way whatsoever.

EXAMPLE 1

17α-(2-carboxyethyl)-17β-hydroxyandrost-4-en-3-one lactone.

To a solution of 0.154 ml of diisopropyl amine in 1 ml of dry ethyl ether at −40° under nitrogen is added 0.68 ml of 1.6 ml butyl lithium in hexane. While maintaining a temperature of −40°, 0.154 ml of 2-diethylamino-2-butenonitrile in 1.5 ml of dry ethyl ether is added dropwise over approximately 30 min. The mixture is stirred at −40° for 30 min, warmed to about −30°, and 150 mg of 3-methoxy-17-oxo-3,5-androstadiene in 2 ml of toluene added dropwise over 30 min (the mixture is stirred at −30° for approximately 30 mins.

The reaction mixture is quenched into pH 7 phosphate buffer, extracted two times with ethylacetate (10 ml.). The organic phase is dried over $Na_2SO_4$ and evaporated to give an oil, the oil is chromatographed on 70 g. of silica gel eluting with 1¼% acetone in methylene chloride and collecting 17α-(2-carboxyethyl)-17β-hydroxyandrost-4-ene-3-one lactone in Fractions 28–35. The nmr spectral analysis is consistent with that obtained on the title compound as prepared by TIMKO, et al. see U.S. Pat. No. 4,211,701.

Fractions 40–80 contain the amino nitrile adduct (II) 17α-[3-(diethylamino)-3-cyano-2-propenyl]-17β-hydroxy-3-methoxy-3,5-androstadiene NMR $(CDCl_3)_3 = 6.47, 5.23, 5.13, 3.57, 2.71, 1.03, 1.00, 0.93 δ MS = 411 (M^+ - 27), 396, 372, 356$ m/e Alternatively the reaction mixture is extracted 3 times with 1N HCl (3×5 ml). The organic phase is washed to neutrality with water, dried over $Na_2SO_4$ and evaporated, yielding unreacted 3-methoxy-17-oxo-3,5-androstadiene. 17α-(2-carboxyethyl)-17β-hydroxyandrost-4-ene-3-one lactone can be isolated from the combined aqueous phases by making basic with 2N NaOH, acidifying to pH 2, extracting with ethylacetate, drying the organic phase with Na$_2$SO$_4$, evaporation to an oil. Crystallization from ethyl acetate gives 17α-(2-carboxyethyl)-17β-hydroxyandrost-4-ene-3-one lactone.

EXAMPLE 2

Dimethyl [1-(diethylamino)-1-propenyl]phosphonate.

200 mM (25.8 g) of N,N-diethyl propionamide is added to 60 ml of methylene chloride (saturated with dry HCl) and phosgene is added as a gas while keeping the temperature below 20°. The addition is accompanied by vigorous evolution of carbon dioxide. When carbon dioxide evolution ceases, the reaction is complete and the solution of imino chloride 2 ($R_x=R_y$=ethyl) can be stored at room temperature.

Following evaporation of the methylene chloride from 2.37 ml (5 mM) of the imino chloride 2 solution, 5 ml of THF is added and the mixture cooled to 0°, followed by dropwise addition of 1.2 ml of trimethyl phosphite (10 mM) in 3 ml of THF, gives, after 30 min, a precipitate of dimethyl [1-(diethylamino)-1-propenyl]-phosphonate hydrochloride. The supernatant is decanted, and 0.7 ml (5 mM) of triethylamine in 5 ml of ether is added to the di-methyl [1-(diethylamino)-1-propenyl]phosphonate hydrochloride. After one hour of vigorous stirring the solid-diethylamine hydrochloride is removed by filtration, the solvent evaporated and the residual oil distilled at 70° C. (1 mm pressure) to give dimethyl [1-(diethylamino)-1-propenyl]-phosphonate.

NMR(CDCl$_3$)=6.45, 3.74, 3.64, 2.87, 1.80, 0.97δ.MS$^+$=221,204,192,112m/e

EXAMPLE 3

17α-[3-(diethylamino)-3-(dimethoxyphosphinyl)-2-propenyl]-17β-hydroxy-3-methoxy-3,5-androstadiene.

A solution of 0.68 ml of 1.6M n-butyllithium in hexane is added to 1 ml of THF and 0.155 ml diisopropylamine at a temperature less than 0°. To this solution at −78° is added dropwise 210 mg (0.95 mM) of dimethyl [1-(diethylamino)-1-propenyl]phosphonate (Example 2) in 1.5 ml of THF giving a red-orange solution of the lithium anion of the foregoing phosphonate. 150 mg. of 3-methoxy-17-oxo-3,5-androstadiene in 1.5 ml of THF is added dropwise over 30 minutes while maintaining the reaction at −78°. The reaction mixture is maintained with stirring at −78° for approximately 8 hours, gradually warmed to room temperature, quenched into ph 7 potassium phosphate buffer, extracted with ethyl acetate, which was dried over sodium sulfate and evaporated under reduced pressure yielding an oil which is chromatographed on 30 g. of silica gel eluting with ethyl acetate to give the title compound, 17α[3-(diethylamino)-3-(dimethoxyphosphinyl)-2-propenyl]17β-hydroxy-3-methoxy-3,5-androstadiene.

NMR(CDCl$_3$)=6.67, 5.21, 5.15, 3.77, 3.66, 3.60, 2.88, 1.20, 1.00, 0.99δ.

Example 3 is reacted at 70° with 2 hydrochloric acid or 50% aqueous acetic acid to give 17-spirolactone.

CHART A

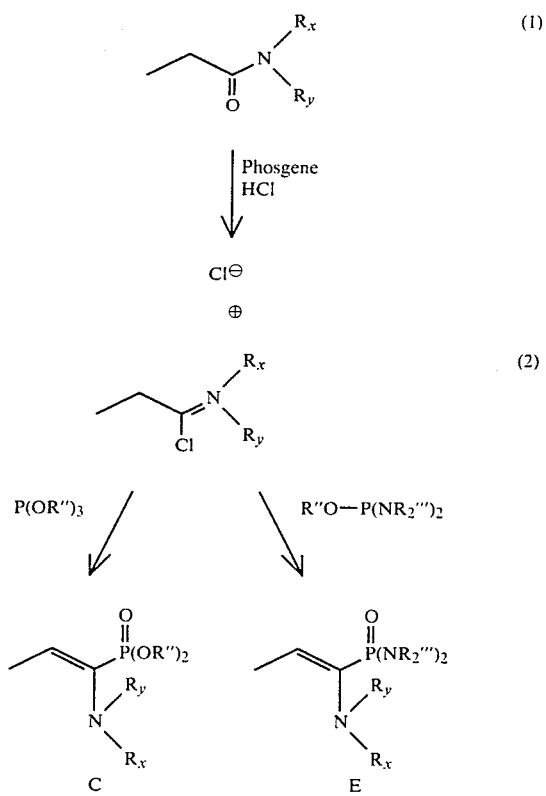

CHART B

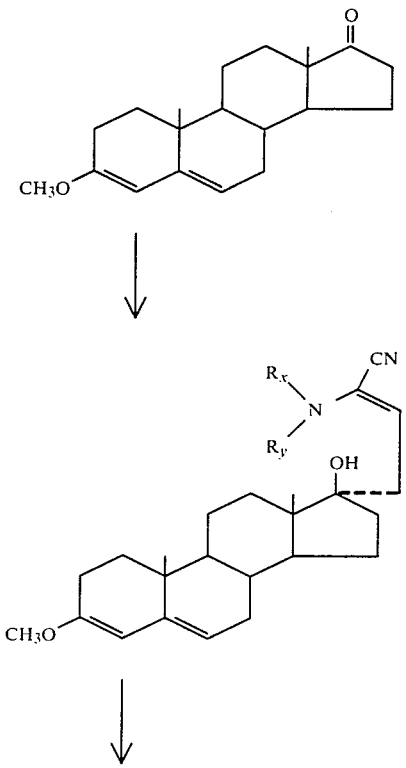

CHART B -continued
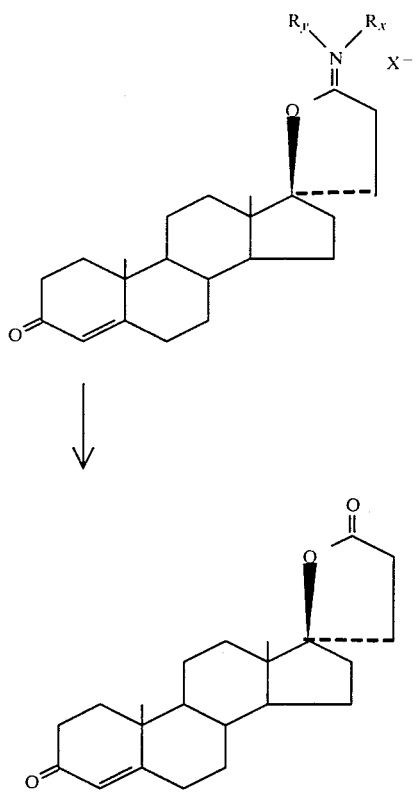
CHART C
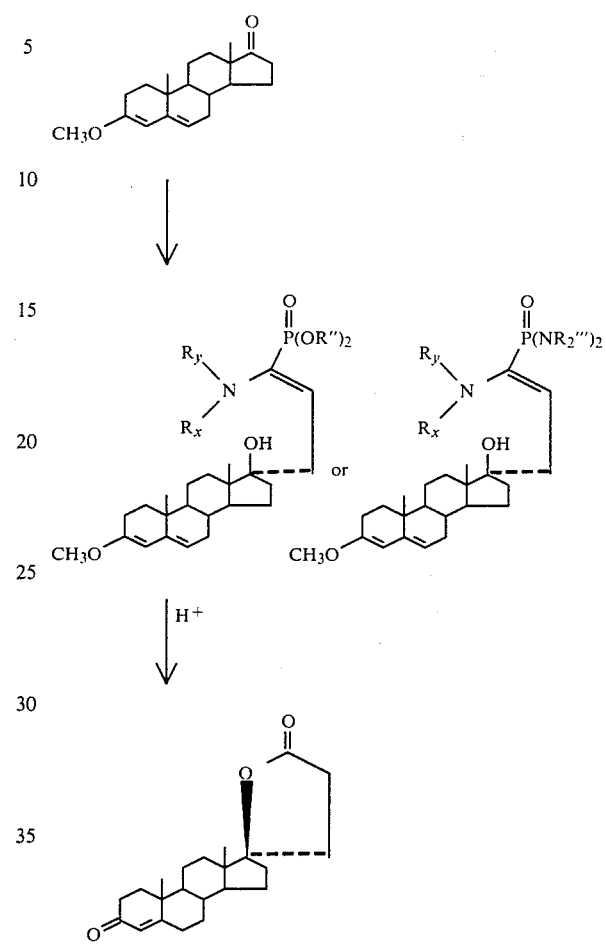
FORMULAS
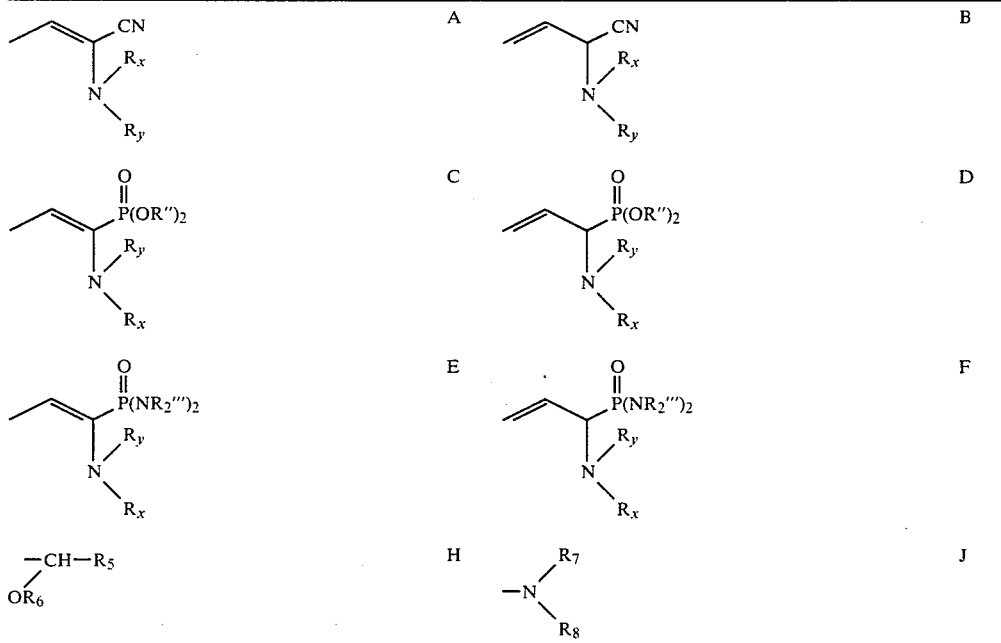

-continued
FORMULAS
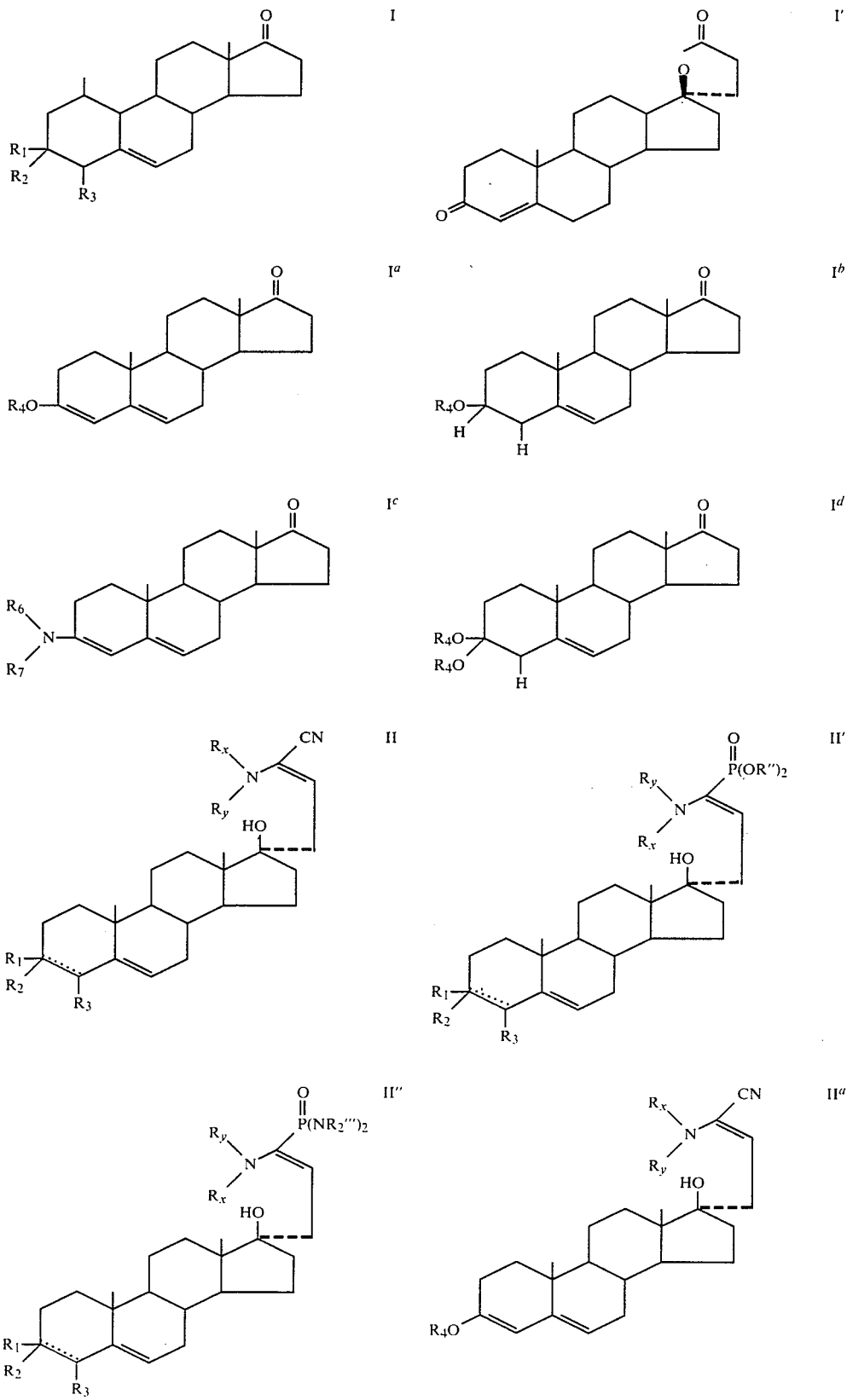

-continued
FORMULAS
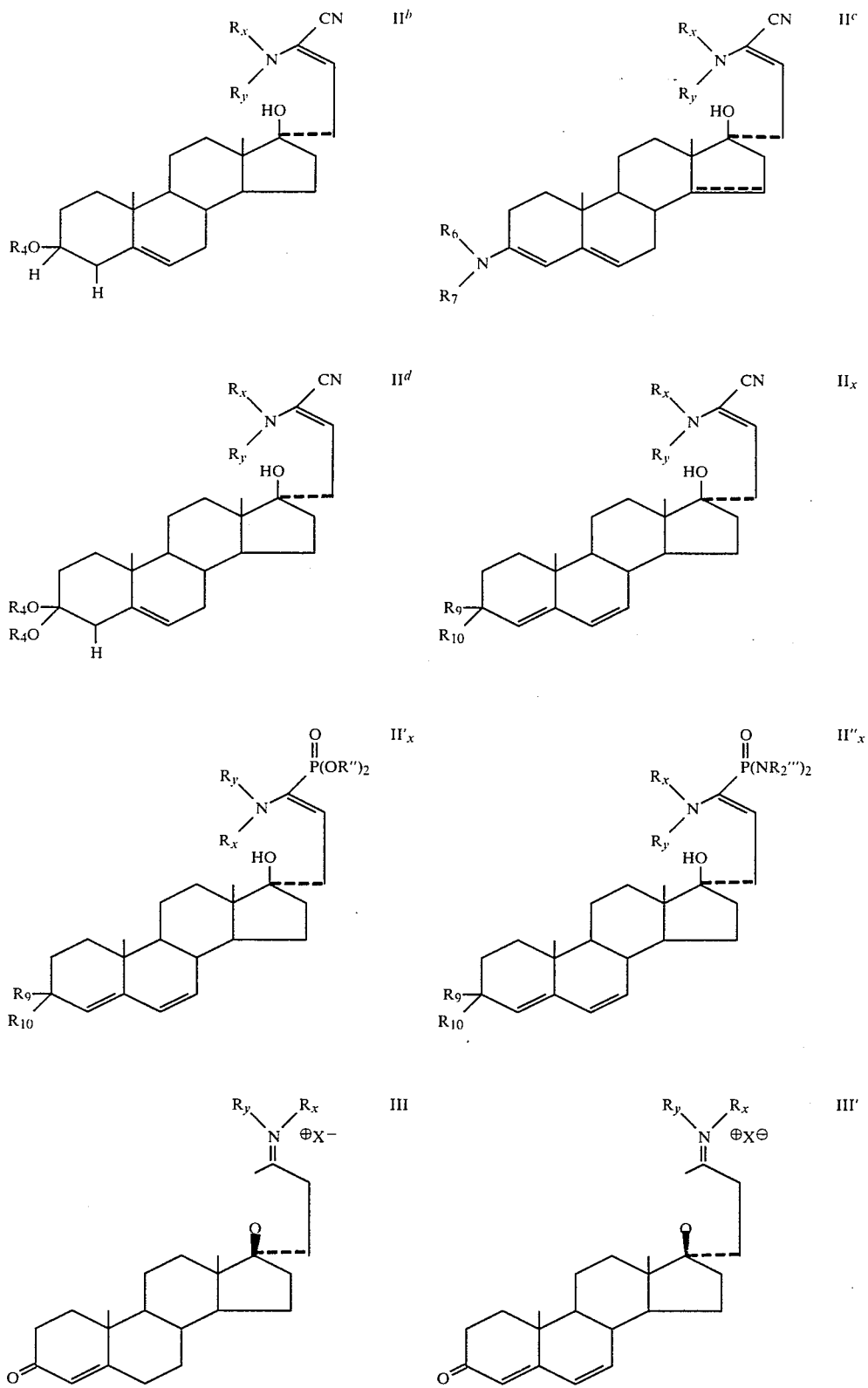

-continued
FORMULAS

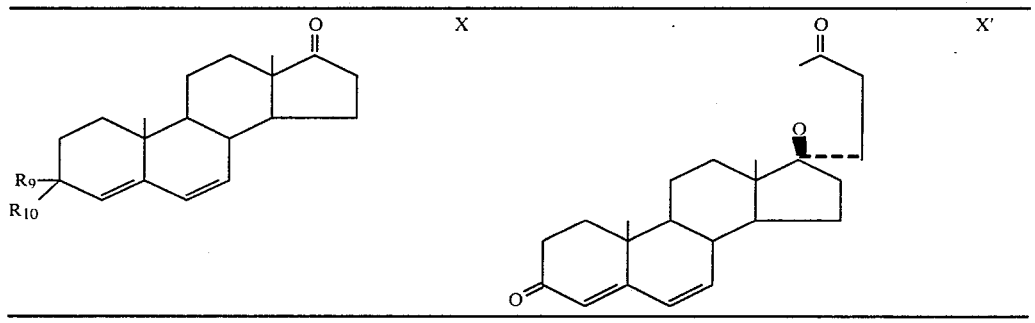

I claim:
1. A compound of formula II

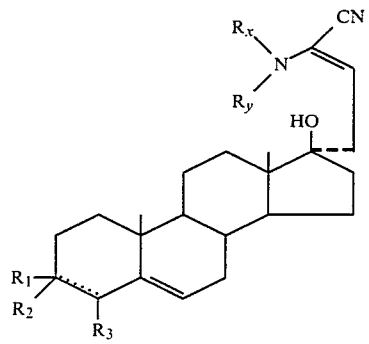

wherein
(i) $R_1$ represents a group $-OR_4$ in which $R_4$ represents a hydrogen atom, an alkyl or alkoxyalkyl group or a $$-\underset{\underset{OR_6}{|}}{CH}-R_5,$$

wherein $R_5$ represents a hydrogen atom or an alkyl group and $R_6$ represents an alkyl group or $R_5$ and $R_6$ together with the carbon and oxygen atoms in which they are attached represent a 5- or 6-membered heterocyclic group, and $R_2$ and $R_3$ each represent a hydrogen atom; or (ii) $R_1$ and $R_2$ are the same or different and each represents a group $-OR_4$, wherein $R_4$ represents an alkyl group, or $R_1$ and $R_2$ together represent an alkylendioxy group having 2 or 3 carbon atoms in the alkylene moiety, and $R_3$ represents a hydrogen atom; or (iii) $R_1$ represents a group $-OR_4$, or a group

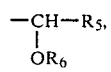

wherein $R_7$ and $R_8$ are the same or different and each represents an alkyl group, or $R_7$ and $R_8$ together with the nitrogen atom to which they are attached represent a 5- or 6-membered heterocyclic group, which may contain a further hetero atom in the ring, and $R_2$ and $R_3$ together represent an additional bond in the 3-4 position; $R_x$ and $R_y$ are the same or different and each represents alkyl of 1 to 5 carbon atoms, aryl of 6 thru 10 carbon atoms or substituted aryl, or $R_x$ and $R_y$ taken together form a 5-, 6- or 7-membered heterocyclic group, which may contain in the ring further hetero atom, selected from the group consisting of nitrogen, oxygen or sulfur.

2. A compound according to claim 1 wherein $R_1$ represents a group $-OR_4$ in which $R_4$ is alkyl of 1 thru 5 carbon atoms, and $R_2$ and $R_3$ each represent a hydrogen atom.

3. A compound according to claim 1 where $R_1$ represents a group $-OR_4$ in which $R_4$ is alkyl of 1 thru 5 carbon atoms, and $R_2$ and $R_3$ together represent an additional bond in the 3-4 position.

4. A compound according to claim 3 wherein $R_1$ represents a group $-OR_4$ in which $R_4$ is methyl and $R_x$ and $R_y$ are each ethyl so that the specific embodiment is 17α-[3-(diethylamino)-3-cyano-2-propenyl]-17β-hydroxy-3-methoxy-3,5-androstadiene.

5. A compound according to claim 1 where $R_1$ represents a group

wherein $R_7$ and $R_8$ are the same or different and each represents an alkyl group of 1 thru 5 carbon atoms, and $R_2$ and $R_3$ together represent an additional bond in the 3-4 position.

6. A compound according to claim 1 where $R_1$ represents a group

wherein $R_7$ and $R_8$ together with the nitrogen atom to which they are attached represent a 5- or 6-membered heterocyclic group, which may contain a further hetero atom in the ring selected from the group consisting of oxygen, nitrogen or sulfur, and $R_2$ and $R_3$ together represent an additional bond in the 3-4 position.

7. A compound according to claim 1 wherein $R_1$ and $R_2$ together represent an alkylendioxy group having 2 or 3 carbon atoms in the alkylene moiety, and $R_3$ represents a hydrogen atom.

8. A compound according to claim 7 where the alkylendioxy group is ethylenedioxy.

9. A compound according to claim 1 wherein $R_1$ and $R_2$ are the same or different and each represents a group $-OR_4$ in which $R_4$ is alkyl of 1 thru 5 carbon atoms, and $R_3$ represents a hydrogen atom.

10. A compound of formula II′

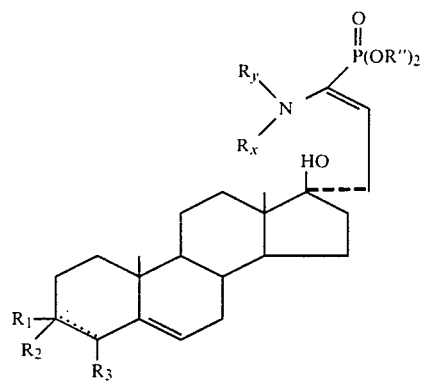

wherein
(i) $R_1$ represents a group $-OR_4$ in which $R_4$ represents a hydrogen atom, an alkyl or alkoxyalkyl group or a

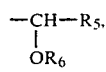

wherein $R_5$ represents a hydrogen atom or an alkyl group and $R_6$ represents an alkyl group or $R_5$ and $R_6$ together with the carbon and oxygen atoms in which they are attached represent a 5- or 6-membered heterocyclic group, and $R_2$ and $R_3$ each represent a hydrogen atom; or (ii) $R_1$ and $R_2$ are the same or different and each represents a group $-OR_4$, wherein $R_4$ represents an alkyl group, or $R_1$ and $R_2$ together represent an alkylendioxy group having 2 or 3 carbon atoms in the alkylene moiety, and $R_3$ represents a hydrogen atom; or (iii) $R_1$ represents a group $-OR_4$, or a group

wherein $R_7$ and $R_8$ are the same or different and each represents an alkyl group, or $R_7$ and $R_8$ together with the nitrogen atom to which they are attached represent a 5- or 6-membered heterocyclic group, which may contain a further hetero atom in the ring, and $R_2$ and $R_3$ together represent an additional bond in the 3–4 position; R″, $R_x$ and $R_y$ are the same or different and each represents alkyl of 1 to 5 carbon atoms, aryl of 6 thru 10 carbon atoms or substituted aryl, or $R_x$ and $R_y$ or R″ and R″ taken together form a 5-, 6- or 7-membered heterocyclic group, which may contain in the ring further hetero atom, selected from the group consisting of nitrogen, oxygen or sulfur.

11. A compound according to claim 10 wherein $R_1$ represents a group $-OR_4$ in which $R_4$ is methyl, $R_x$ and $R_y$ are each ethyl, and R″ is methyl so that the specific embodiment is 17α-[3-(diethylamino)-3-(dimethoxyphosphinyl)-2-propenyl]-17β-hydroxy-3-methoxy-3,5-androstadiene.

12. A compound of formula II″

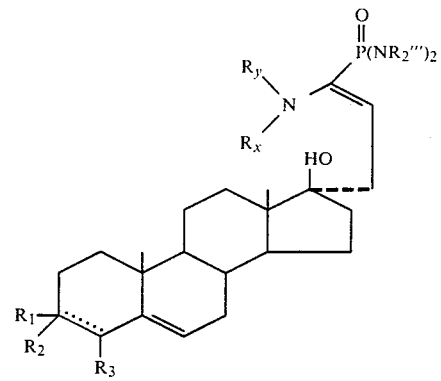

wherein
(i) $R_1$ represents a group $-OR_4$ in which $R_4$ represents a hydrogen atom, an alkyl or alkoxyalkyl group or a

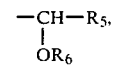

wherein $R_5$ represents a hydrogen atom or an alkyl group and $R_6$ represents an alkyl group or $R_5$ and $R_6$ together with the carbon and oxygen atoms in which they are attached represent a 5- or 6-membered heterocyclic group, and $R_2$ and $R_3$ each represent a hydrogen atom; or (ii) $R_1$ and $R_2$ are the same or different and each represents a group $-OR_4$, wherein $R_4$ represents an alkyl group, or $R_1$ and $R_2$ together represent an alkylendioxy group having 2 or 3 carbon atoms in the alkylene moiety, and $R_3$ represents a hydrogen atom; or (iii) $R_1$ represents a group $-OR_4$, or a group

wherein $R_7$ and $R_8$ are the same or different and each represents an alkyl group, or $R_7$ and $R_8$ together with the nitrogen atom to which they are attached represent a 5- or 6-membered heterocyclic group, which may contain a further hetero atom in the ring, and $R_2$ and $R_3$ together represent an additional bond in the 3–4 position; $R_x$ and $R_y$ are the same or different and each represents alkyl of 1 to 5 carbon atoms, aryl of 6 thru 10 carbon atoms or substituted aryl, or $R_x$ and $R_y$ or R‴ and R‴ taken together form a 5-, 6- or 7-membered heterocyclic group, which may contain in the ring further hetero atom, selected from the group consisting of nitrogen, oxygen or sulfur.

13. A compound of the formula:

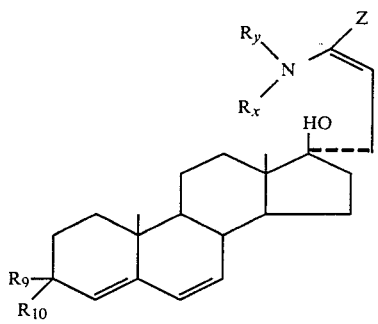

wherein Z is selected from

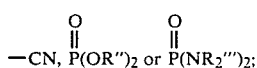

$R_9$ and $R_{10}$ together represent an alkylenedioxy group having 2 or 3 carbon atoms in the alkylene moiety; and R", R''', $R_x$ and $R_y$ are the same or different and each represents alkyl of 1 to 5 carbon atoms, aryl of 6 thru 10 carbon atoms or substituted aryl, or $R_x$ and $R_y$ or R" and R" or R''' and R''' taken together form a 5-, 6- or 7-membered heterocyclic group, which may contain in the ring a further hetero atom, selected from the group consisting of nitrogen, oxygen or sulfur.

14. A process for the preparation of 17α-(2-carboxyethyl)-17β-hydroxy-androst-4-en-3-one lactone and 17α-(2-carboxyethyl)-17β-hydroxy-androsta-4,6-diene-3-one lactone of the formula I':

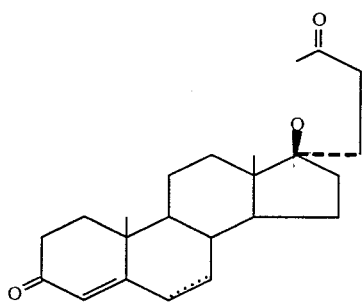

wherein the dotted line between the 6–7 positions indicates the additional double bond of the latter compound, which comprises:

(1) treating a disubstituted amino nitrile of formula A

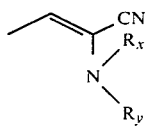

where $R_x$ and $R_y$ are the same or different and each represents alkyl of 1 to 5 carbon atoms, aryl of 6 thru 10 carbon atoms or substituted aryl, or $R_x$ and $R_y$ taken together form a 5-, 6- or 7-membered heterocyclic group, which may contain in the ring a further hetero atom, selected from the group consisting of nitrogen, oxygen or sulfur, with an alkali metal amide deprotonating agent;

(2) reacting the resultant deprotonated nitrile with a 3-protected androst-5-ene-17-one derivative of formula I:

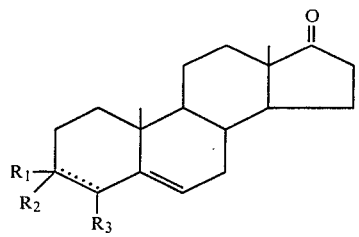

wherein (i) $R_1$ represents a group —$OR_4$ in which $R_4$ represents a hydrogen atom, an alkyl or alkoxyalkyl group or a

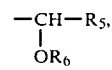

wherein $R_5$ represents a hydrogen atom or an alkyl group and $R_6$ represents an alkyl group or $R_5$ and $R_6$ together with the carbon and oxygen atoms in which they are attached represent a 5- or 6-membered heterocyclic group and $R_2$ and $R_3$ each represent a hydrogen atom; or (ii) $R_1$ and $R_2$ are the same or different and each represents a group —$OR_4$, wherein $R_4$ represents an alkyl group, or $R_1$ and $R_2$ together represent an alkylenedioxy group having 2 or 3 carbon atoms in the alkylene moiety, and $R_3$ represents a hydrogen atom;

(iii) $R_1$ represents a group —$OR_4$, or a group

wherein $R_7$ and $R_8$ are the same or different and each represents an alkyl group, or $R_7$ and $R_8$ together with the nitrogen atom to which they are attached represent a 5- or 6-membered heterocyclic group, which may contain a further hetero atom in the ring and $R_2$ and $R_3$ together represent an additional bond in the 3-4 position; to give the amino nitrile adduct (II)

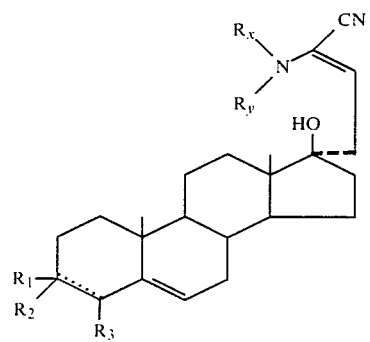

where $R_1$, $R_2$, $R_3$, $R_x$ and $R_y$ are as hereinbefore defined;

(3) acidifying the amino nitrile adduct (II) with an acid to form the imino lactone (III); and

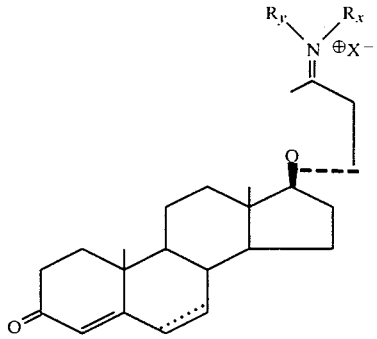

(4) neutralizing the imino lactone (III) by reaction with a base to give a 17-spiro-γ-lactone of formula I'.

15. A process according to claim 14 where the deprotonating agent is selected from the group consisting of lithium diisopropylamide, lithium diethylamide, lithium hexamethyldisilazide or the sodium or potassium salts of the foregoing amides.

16. A process according to claim 14 where the deprotonating agent is lithium diisopropylamide.

17. A process according to claim 14 where the steroidal-17-ketone (I) is selected from the group consisting of 3-methoxy-, 3-ethoxy-, 3-propoxy or 3-butoxy-17-oxo-3,5-androstadiene.

18. A process according to claim 14 where the steroidal-17-ketone (I) is 3-methoxy-17-oxo-3,5-androstadiene.

19. A process according to claim 15 where the steroidal-17-ketone (I) is selected from the group consisting of 3-methoxy-, 3-ethoxy-, 3-propoxy or 3-butoxy-17-oxo-3,5-androstadiene.

20. A process according to claim 16 where the steroidal-17-ketone (I) is 3-methoxy-17-oxo-3,5-androstadiene.

21. A process according to claim 19 where the disubstituted amino nitrile is selected from the group consisting of 2-dimethylamino-3-butenonitrile, 2-diethylamino-3-butenonitrile, 2-(1'-pyrrolidino)-3-butenonitrile, 2-(1'-piperidino)-3-butenonitrile, 2-(N-morpholino)-3-butenonitrile or N-methylanilino-3-butenonitrile.

22. A process according to claim 14 where the disubstituted amino nitrile is 2-diethylamino-2-butenonitrile.

23. A process according to claim 15 where the disubstituted amino nitrile is 2-diethylamino-2-butenonitrile.

24. A process according to claim 16 where the disubstituted amino nitrile is 2-diethylamino-2-butenonitrile.

25. A process according to claim 17 where the disubstituted amino nitrile is 2-diethylamino-2-butenonitrile.

26. A process according to claim 18 where the disubstituted amino nitrile is 2-diethylamino-2-butenonitrile.

27. A process according to claim 19 where the disubstituted amino nitrile is 2-diethylamino-2-butenonitrile.

28. A process according to claim 20 where the disubstituted amino nitrile is 2-diethylamino-2-butenonitrile.

29. A process for the preparation of 17α-(2-carboxyethyl)-17β-hydroxy-androst-4-en-3-one lactone and 17α-(2-carboxyethyl)-17β-hydroxy-androsta-4,6-diene-3-one lactone of the formula I':

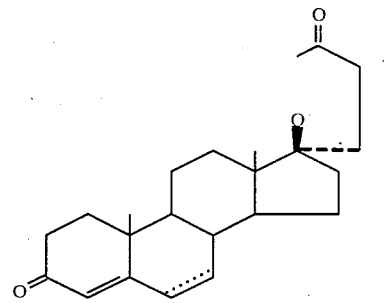

wherein the dotted line between the 6–7 positions indicates the additional double bond of the latter compound which comprises:

(1) treating a disubstituted phosphonate enamine selected from

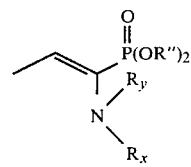   C or

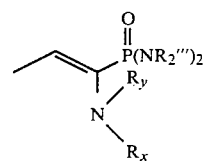   E wherein R'', R''', $R_x$ and $R_y$ are the same or different and each represents alkyl of 1 to 5 carbon atoms, aryl of 6 thru 10 carbon atoms or substituted aryl, or $R_x$ and $R_y$ or R'' and R'' or R''' and R''' taken together form a 5-, 6- or 7-membered heterocyclic group, which may contain in the ring a further hetero atom, selected from the group consisting of nitrogen, oxygen or sulfur, with an alkali metal amide deprotonating agent;

(2) reacting the resultant deprotonated enamine with a 3-protected androst-5-ene-17-one derivative of formula I:

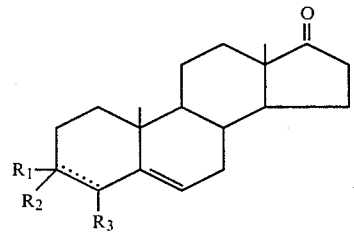

wherein (i) $R_1$ represents a group —$OR_4$ in which $R_4$ represents a hydrogen atom, an alkyl or alkoxyalkyl group or a

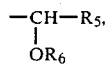

wherein R₅ represents a hydrogen atom or an alkyl group and R₆ represents an alkyl group or R₅ and R₆ together with the carbon and oxygen atoms in which they are attached represent a 5- or 6-membered heterocyclic group and $R_2$ and $R_3$ each represent a hydrogen atom; or (ii) $R_1$ and $R_2$ are the same or different and each represents a group —OR₄, wherein R₄ represents an alkyl group, or $R_1$ and $R_2$ together represent an alkylenedioxy group having 2 or 3 carbon atoms in the alkylene moiety, and $R_3$ represents a hydrogen atom;

(iii) $R_1$ represents a group —OR₄, or a group

wherein $R_7$ and $R_8$ are the same or different and each represents an alkyl group, or $R_7$ and $R_8$ together with the nitrogen atom to which they are attached represent a 5- or 6-membered heterocyclic group, which may contain a further hetero atom in the ring and $R_2$ and $R_3$ together represent an additional bond in the 3–4 position to give the corresponding phosphonate enamine adduct (II′ or II″):

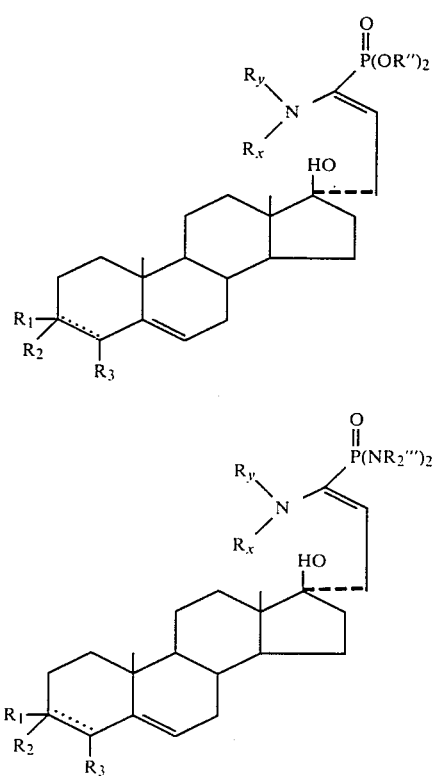

where $R_1$, $R_2$, $R_3$, $R_x$, $R_y$, R″, R‴ are as hereinbefore defined;

(3) acidifying the phosphonate enamine adduct (II′ or II″) with an acid to give a spiro-γ-lactone of formula I′.

30. A process according to claim 29 where the deprotonating agent is selected from the group consisting of lithium diisopropylamide, lithium diethylamide, lithium hexamethyldisilazide or the sodium or potassium salts of the foregoing amides.

31. A process according to claim 29 where the deprotonating agent is lithium diisopropylamide.

32. A process according to claim 29 where the steroidal-17-ketone (I) is selected from the group consisting of 3-methoxy-, 3-ethoxy-, 3-propoxy or 3-butoxy-17-oxo-3,5-androstadiene.

33. A process according to claim 29 where the steroidal-17-ketone (I) is 3-methoxy-17-oxo-3,5-androstadiene.

34. A process according to claim 30 where the steroidal-17-ketone (I) is selected from the group consisting of 3-methoxy-, 3-ethoxy-, 3-propoxy or 3-butoxy-17-oxo-3,5-androstadiene.

35. A process according to claim 31 where the steroidal-17-ketone (I) is 3-methoxy-17-oxo-3,5-androstadiene.

36. A process according to claim 29 where the disubstituted phosphonate enamine is selected from the group consisting of dimethyl[1-(diethylamino)-1-propenyl]phosphonate, p-[1-(diethylamino)-1-propenyl]-N,N,N′,N′-tetramethylphosphonic diamide, dimethyl[1-(1′-pyrrolidino)-1-propenyl]phosphonate, p-[1-(1′-pyrrolidino)-1-propenyl]-N,N,N′,N′-tetramethylphosphonic diamide, dimethyl[1-(1′-piperidino)-1-propenyl]-phosphonate, p-[1-(1′-piperidino)-1-propenyl]-N,N,N′,N′-tetramethylphosphonic amide, dimethyl[1-(N-morpholino)-1-propenyl]phosphonate, p-[1-(N-morpholino)-1-propenyl]-N,N,N′,N′-tetramethylphosphonic diamide, dimethyl[1-(N-methylanilino)-1-propenyl]phosphonate, p-[1-(N-methylanilino)-1-propenyl]-N,N,N′,N′-tetramethylphosphonic diamide.

37. A process according to claim 29 where the disubstituted phosphonate enamine is dimethyl[1-(diethylamino)-1-propenyl]phosphonate.

38. A process according to claim 30 where the disubstituted phosphonate enamine is dimethyl[1-(diethylamino)-1-propenyl]phosphonate.

39. A process according to claim 31 where the disubstituted phosphonate enamine is dimethyl[1-(diethylamino)-1-propenyl]phosphonate.

40. A process according to claim 32 where the disubstituted phosphonate enamine is dimethyl[1-(diethylamino)-1-propenyl]phosphonate.

41. A process according to claim 33 where the disubstituted phosphonate enamine is dimethyl[1-(diethylamino)-1-propenyl]phosphonate.

42. A process according to claim 34 where the disubstituted phosphonate enamine is dimethyl[1-(diethylamino)-1-propenyl]phosphonate.

43. A process according to claim 35 where the disubstituted phosphonate enamine is dimethyl[1-(diethylamino)-1-propenyl]phosphonate.

44. A process for the preparation of 17α-(2-carboxyethyl)-17β-hydroxy-androsta-4,6-diene-3-one lactone of the formula X′

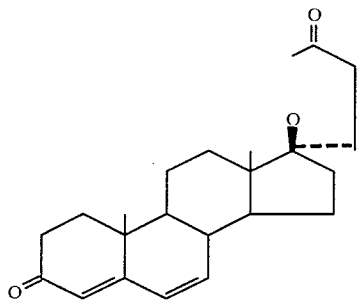

which comprises:
(1) treating a disubstituted amino nitrile of formula A

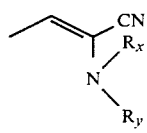

where $R_x$ and $R_y$ are the same or different and each represents alkyl of 1 to 5 carbon atoms, aryl of 6 thru 10 carbon atoms or substituted aryl, or $R_x$ and $R_y$ taken together form a 5-, 6- or 7-membered heterocyclic group, which may contain in the ring a further hetero atom, selected from the group consisting of nitrogen, oxygen or sulfur, with an alkali metal amide deprotonating agent;
(2) reacting the resultant deprotonated nitrile with a 3-ketal androsta-4,6-diene-17-one derivative of formula X:

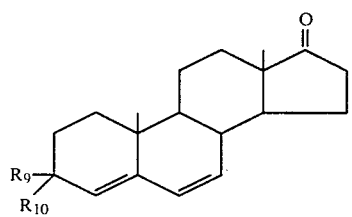

wherein $R_9$ and $R_{10}$ together represent an alkylenedioxy group having 2 or 3 atoms in the alkylene moiety; to give the amino nitrile adduct $(II_x)$

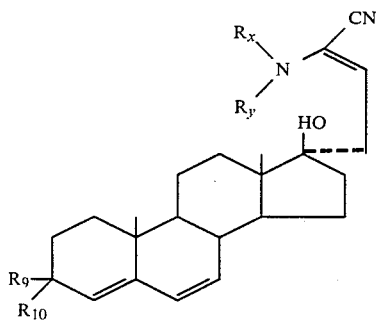

where $R_9$, $R_{10}$, $R_x$ and $R_y$ are as hereinbefore defined;
(3) acidifying the amino nitrile adduct $(II_x)$ with an acid to form the imino lactone

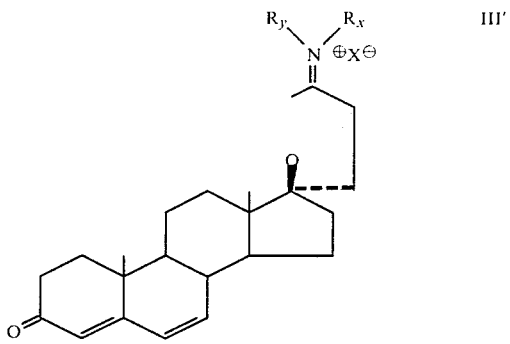

(4) neutralizing the imino lactone (III') by reaction with a base to give a 17-spiro-γ-lactone of formula X'.

45. A process for the preparation of 17α-(2-carboxyethyl)-17β-hydroxy-androsta-4,6-diene-3-one lactone of the formula X':

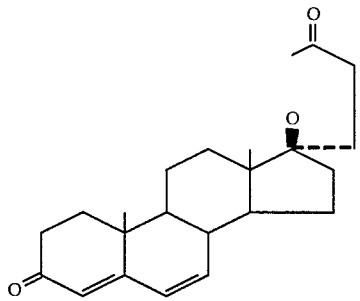

(1) treating a disubstituted phosphonate enamine selected from

C or

E wherein R", R''', $R_x$ and $R_y$ are the same or different and each represents alkyl of 1 to 5 carbon atoms, aryl of 6 thru 10 carbon atoms or substituted aryl, or $R_x$ and $R_y$ taken together form a 5-, 6- or 7-membered heterocyclic group, which may contain in the ring a further
hetero atom, selected from the group consisting of nitrogen, oxygen or sulfur, with an alkali metal amide deprotonating agent;
(2) reacting the resultant deprotonated enamine with a 3-ketal androst-5-ene-17-one derivative of formula X:

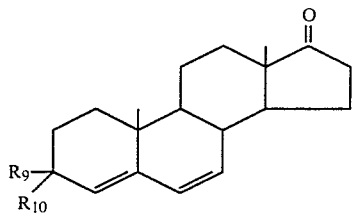
wherein $R_9$ and $R_{10}$ together represent an alkylenedioxy group having 2 or 3 atoms in the alkylene moiety; to give the corresponding phosphonate enamine adduct ($II'_x$ and $II''_x$)
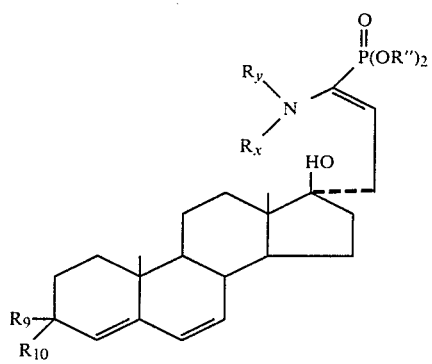
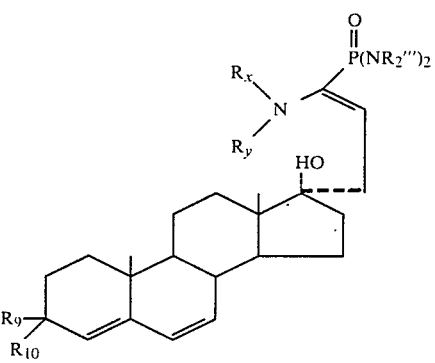
where $R_9$, $R_{10}$, $R_x$, $R_y$, $R''$, and $R'''$ are as hereinbefore defined;
(3) acidifying the phosphonate enamine adduct ($II'_x$ or $II''_x$) with an acid to give a spiro-γ-lactone of formula $X'$.
* * * * *

UNITED STATES PATENT OFFICE
CERTIFICATE OF CORRECTION

Patent No. 4,501,695    Dated 26 February 1985

Inventor(s) E.H. VanRheenen

It is certified that error appears in the above-identified patent and that said Letters Patent are hereby corrected as shown below:

Column 3, line 63:  "or R" and R''' and R''' " should read -- or R" and R" or R''' and R''' --.

Column 5, lines 38-39:  "phosphonyl" should read -- phosphinyl --.

Column 12, formula I': 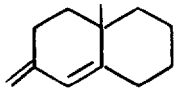 should read -- 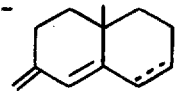 --.

Column 13, (portion of formula III): " ⊕  X  " should read -- ⊕  X  ⊖ --.

Column 21, line 7: " ⊕  X  " should read -- ⊕  X  ⊖ --.

Column 21, line 45 (Claim 21): "A process according to claim 19" should read -- A process according to Claim 14 --.

Signed and Sealed this

Seventeenth Day of June 1986

[SEAL]

Attest:

DONALD J. QUIGG

Attesting Officer    Commissioner of Patents and Trademarks